US012746116B2

(12) United States Patent
Lalieu et al.

(10) Patent No.: US 12,746,116 B2
(45) Date of Patent: Sep. 29, 2026

(54) REINFORCED HEART VALVE LEAFLETS

(71) Applicant: Xeltis, B.V., Eindhoven (NL)

(72) Inventors: Roland Lambertus Joannes Lalieu, Weert (NL); Martijn Antonius Johannes Cox, Budel (NL)

(73) Assignee: Xeltis AG, Zurich (CH)

( * ) Notice: Subject to any disclaimer, the term of this patent is extended or adjusted under 35 U.S.C. 154(b) by 613 days.

(21) Appl. No.: 18/265,326

(22) PCT Filed: Dec. 6, 2021

(86) PCT No.: PCT/EP2021/084381
§ 371 (c)(1),
(2) Date: Jun. 5, 2023

(87) PCT Pub. No.: WO2022/122647
PCT Pub. Date: Jun. 16, 2022

(65) Prior Publication Data

US 2024/0033076 A1 Feb. 1, 2024

Related U.S. Application Data

(60) Provisional application No. 63/124,289, filed on Dec. 11, 2020.

(51) Int. Cl.
*A61F 2/24* (2006.01)

(52) U.S. Cl.
CPC .... *A61F 2/2415* (2013.01); *A61F 2210/0004* (2013.01)

(58) Field of Classification Search
CPC .. A61F 2/2415; A61F 2210/0004; A61F 2/24; A61F 2/2418; A61F 2/2412
See application file for complete search history.

(56) References Cited

U.S. PATENT DOCUMENTS

| | | | |
|---|---|---|---|
| 9,463,082 | B2 | 10/2016 | O'hare |
| 10,149,749 | B2 | 12/2018 | MacEwan |
| 11,129,711 | B2 * | 9/2021 | Badhwar .............. A61F 2/2418 |
| 2014/0207250 | A1 | 7/2014 | O'Hare |
| 2015/0230918 | A1 | 8/2015 | Detamore |
| 2015/0297791 | A1 | 10/2015 | Patel |
| 2017/0000610 | A1 | 1/2017 | Eppihimer |
| 2019/0201588 | A1 | 7/2019 | Serrero |
| 2019/0271098 | A1 | 9/2019 | Johnson |
| 2020/0093957 | A1 | 3/2020 | MacNeil |
| 2024/0033076 | A1 * | 2/2024 | Lalieu ................. D01D 5/0069 |

FOREIGN PATENT DOCUMENTS

| | | |
|---|---|---|
| WO | WO2003099230 | 12/2003 |

* cited by examiner

*Primary Examiner* — Bruce E Snow
(74) *Attorney, Agent, or Firm* — LUMEN PATENT FIRM

(57) ABSTRACT

A heart valve with reinforced leaflets is provided. The free edge of the leaflet and/or the leaflet belly area of the leaflet has a circumferentially aligned band of aligned electrospun fibers with non-aligned fibers. The aligned and/or the non-aligned fibers are bioabsorbable polymer fibers, and are capable of being replaced over time with newly formed tissue. A method is provided to make these heart valve leaflets using two sources of electrospinning which electrospun simultaneously to either form distinct layers or intermixed layers of aligned and non-aligned fibers.

10 Claims, 3 Drawing Sheets

REINFORCED HEART VALVE LEAFLETS

FIELD OF THE INVENTION

This invention relates to restorative heart valves.

BACKGROUND OF THE INVENTION

A natural heart valve has a highly-organized tri-layer structure capable of coping with forces placed upon it while being thin and flexible enough to open and close properly. It has three distinct layers, each layer with unique structural and functional properties, and a preferred alignment of tissue fibers beneficial for the performance of the heart valve.

Single layered prosthetic heart valves or restorative heart valves which replace natural heart valves are normally made from pericardium and have limited long term durability. However, artificial scaffolds for heart valves do not adequately mimic the mechanical properties of natural donor scaffolds. During durability tests of the current valve design leaflets tend to rupture, mainly in radial direction. Accordingly, there is a need for a new scaffold material that has a higher durability while still maintaining the desired and needed mobility. The new scaffold should also have aligned reinforcement with different strength in different areas/directions. The present invention provides an electrospinning method specifically designed for heart valves to address at least some of the problems.

SUMMARY OF THE INVENTION

In one embodiment the invention is a method of electrospinning a heart valve leaflet. Aligned fibers are electrospun onto a mandrel using a first source. The aligned fibers are bioabsorbable polymer fibers. Non-aligned fibers are electrospun onto the mandrel using a second source. The second source electospins simultaneously with the first source and, these non-aligned fibers are bioabsorbable polymer fibers. The electrospinning of the aligned fibers includes electrospinning distinct patches or regions at the mandrel therewith producing a circumferentially aligned band of the heart valve leaflet. The aligned fibers and the non-aligned fibers at the distinct patches or regions are electrospun as either distinct layers or as an intermixed pattern. The circumferentially aligned band can be from commissure to commissure at or near the free edge of the heart valve leaflet, or the circumferentially aligned band is used to reinforce a belly area of the heart valve leaflet.

In another embodiment, the invention pertains to a heart valve with at least one leaflet. A free edge of the leaflet comprises or consists essentially of a circumferentially aligned band of aligned electrospun fibers with non-aligned fibers. The aligned fibers are bioabsorbable polymer fibers, the non-aligned fibers are bioabsorbable polymer fibers, and the aligned fibers and the non-aligned fibers at the free edge are either distinct layers or intermixed.

In still another embodiment, the invention pertains to a heart valve with at least one leaflet. The leaflet belly area comprises or consists essentially of a circumferentially aligned band of aligned electrospun fibers with non-aligned fibers. The aligned fibers are bioabsorbable polymer fibers, the non-aligned fibers are bioabsorbable polymer fibers, and the aligned fibers and the non-aligned fibers at the free edge are either distinct layers or intermixed.

In the embodiments, the bioabsorbable polymer fibers of the aligned fibers can be supramolecular bioabsorbable polymer fibers and/or the bioabsorbable polymer fibers of the non-aligned fibers can be supramolecular bioabsorbable polymer fibers.

In the embodiments, the bioabsorbable polymer fibers of the aligned fibers form a porous network to allow infiltration of cells, and the porous network with infiltrated cells is capable of being replaced over time with newly formed tissue, and/or the bioabsorbable polymer fibers of the non-aligned fibers form a porous network to allow infiltration of cells, and the porous network with infiltrated cells is capable of being replaced over time with newly formed tissue.

DETAILED DESCRIPTION

Figure 1:
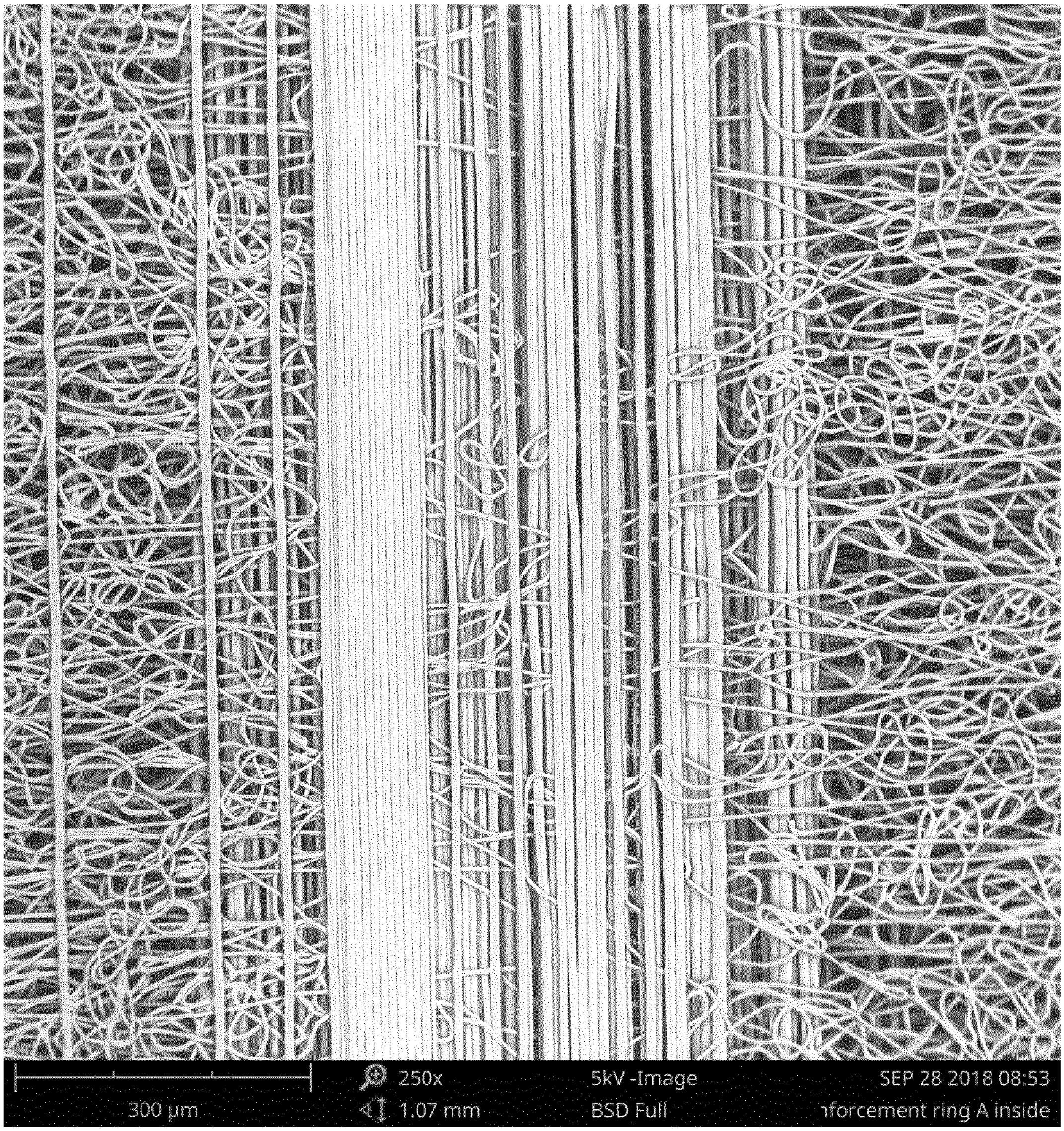
FIG. 1 shows according to an exemplary embodiment of the invention an enforcement ring of aligned fibers (view from outside), spun simultaneously with random fibers, yielding an intertwined pattern.
Figure 2:
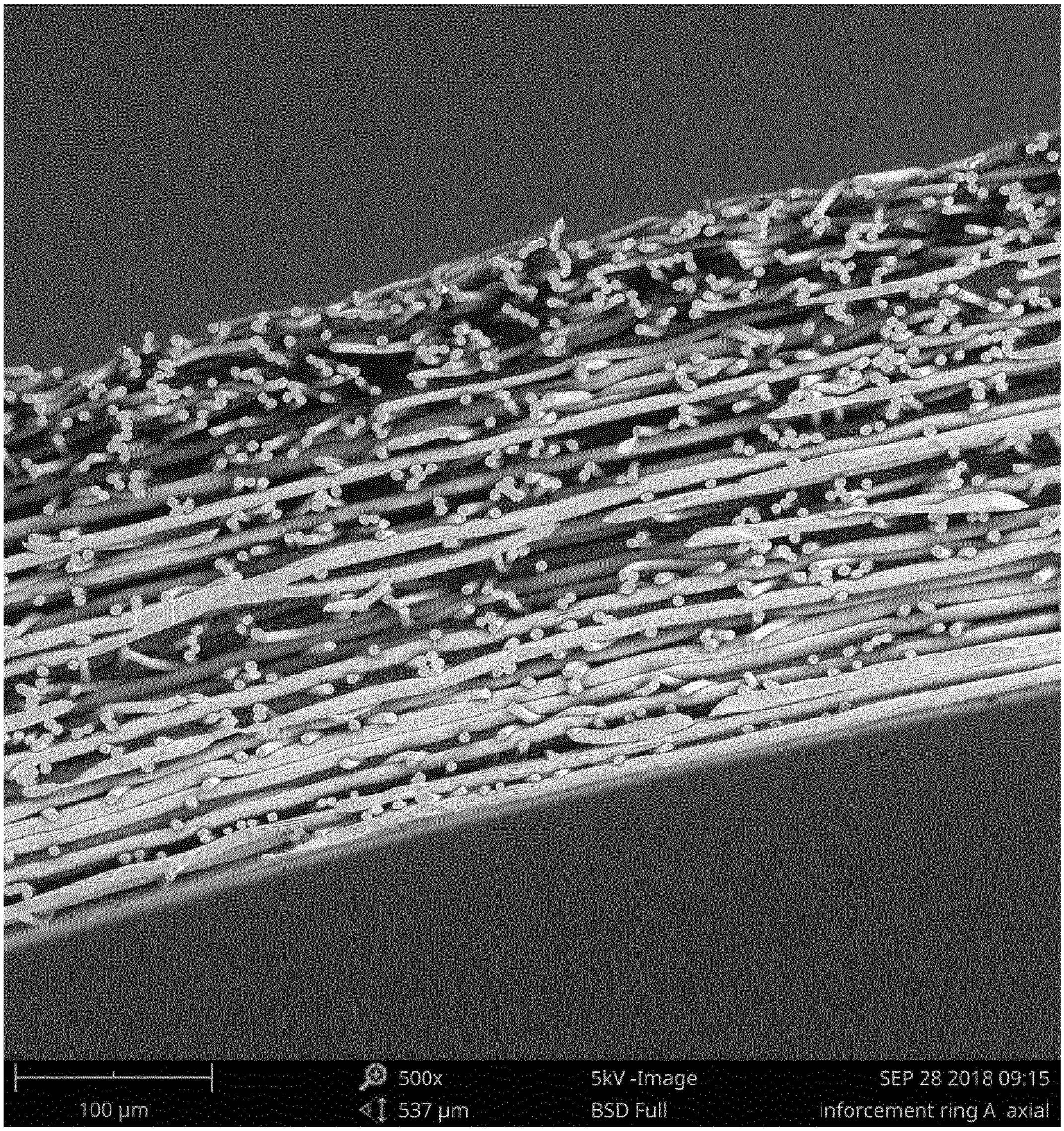
FIG. 2 shows according to an exemplary embodiment of the invention a matrix of aligned fibers alternating with random fibers (sectional view).
Figure 3:
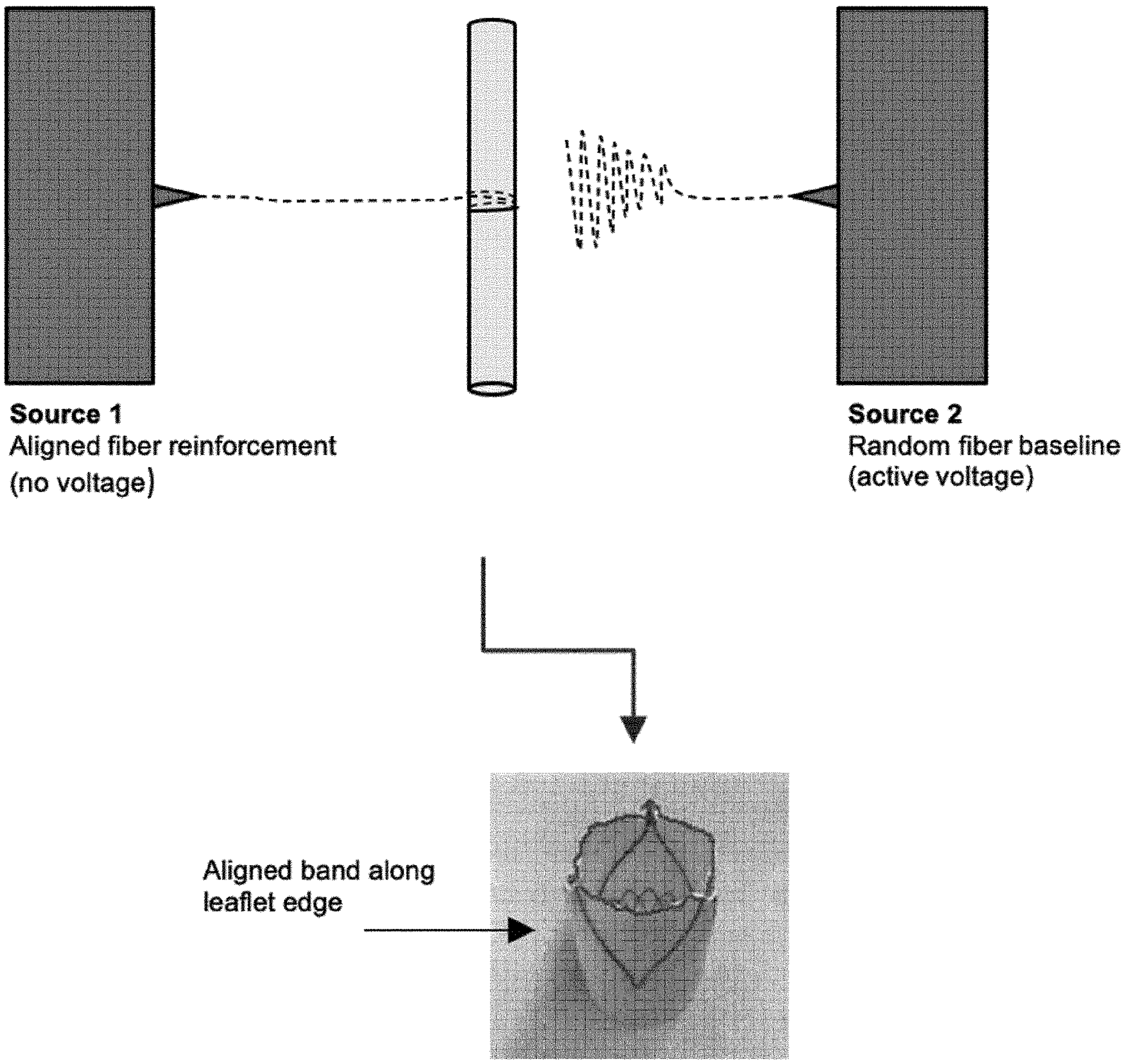
FIG. 3 shows according to an exemplary embodiment of the invention a method of electrospinning using two sources simultaneously with one source for aligned fibers and the other source for non-aligned fibers to form a heart valve.

Embodiments of the invention pertain to a method and a method of making reinforced heart valve leaflets. In one example, the invention is a method of:

- Simultaneous spinning of aligned and non-aligned fibers to form a heart valve that is capable of allowing endogenous tissue restoration (ETR). Simultaneous spinning is capable of creating a microstructure that allows ETR and improves integration and adhesion.
- Simultaneous electrospinning using two sources, where 1 source produces a straight jet and the other source produces random fibers (FIG. 3). The advantage of the straight jet is a more precise control of location of deposition. The advantage of simultaneous electrospinning using two sources is that this ensures (i) better adhesion between aligned and random structures, and (ii) improves porosity by avoiding too dense aligned areas. A straight jet could alternatively be achieved through a kind of melt extrusion process (e.g. electrospinning without voltage difference).
- Creating specific locations of fiber reinforcement of the heart valve, which is achievable due to the precise control of the straight jet. For example, a circumferentially aligned band along the free edge of the heart valve, going from commissure to commissure. In another example, a curvilinear circumferentially aligned set of bands/bundles, running from commissure to commissure. In yet another example, a circumferentially aligned band/bundle in the belly area of a leaflet.
- In one embodiment, the use of supramolecular polymers for this method.

The artificially engineered electrospun heart valve has at least a layer of aligned fibers and at least a layer of randomly oriented fibers. With this approach, it is possible to then generate a heart valve having mechanical properties which more closely match those of a natural donor scaffold with regard to stiffness and strength.

In one embodiment, very directed, aligned fibers are produced, which are intermixed with more randomly oriented "normal" electrospun fibers without creating distinct layers. This leads to a heart valve tissue with aligned and non-aligned fibers that are in direct connection to each other and interwoven.

In another embodiment, aligned fibers are produced in distinct areas to enforce the resulting heart valve tissue. This results in distinct patches or band-like structures that may be alternating with non-aligned fibers.

In yet another embodiment, the aligned fibers are produced simultaneously with non-aligned fibers, thus creating stronger interaction and adhesion between aligned and non-aligned fibers, which is beneficial for preventing delamination, and may provide a more optimal distribution of local porosity (for cell ingrowth and ETR).

In yet another embodiment, the aligned fibers are produced as a straight jet, thus allowing more controlled deposition.

In yet another embodiment, the straight jet to produce aligned fibers is produced through a melt-extrusion process or through an electrospinning process or through a winding process.

In yet another embodiment, the aligned fibers form a circumferentially aligned band along the free edge of a heart valve leaflet, going from commissure to commissure.

In yet another embodiment, the aligned fibers form a curvilinear circumferentially aligned set of bands/bundles, running from commissure to commissure.

In yet another embodiment, the aligned fibers form a circumferentially aligned band/bundle in the belly area of a leaflet.

In yet another embodiment, the aligned fibers would be deposited on a leaflet in bands or bundles to optimize balance between leaflet durability and flexibility. In yet another embodiment, the aligned fibers could have either an absorbable or a non-absorbable material.

In still another embodiment, the aligned fibers could be a suture wire for example made from UltraHigh Molecular Weight PolyEthylene (UHMWPE).

By spinning fibers in a more circumferential direction, these heart valves increase their durability. The aligned fibers could be locally defined or dispersed. Alignment could be done in a preferred direction e.g. reinforcement into the circumferential direction could be preferred since forces onto the leaflet in the circumferential direction are bigger and could therefore lead to failure of the leaflet. The area of aligned fibers could be locally defined or dispersed over the whole area, aligned in a preferred direction and/or dispersed as patches or along the whole scaffold. By this approach leaflets could be reinforced and are more durable as a result. They could be reinforced by aligned fibers in different ways such as (bio-absorbable) wire, locally aligned fibers or a band.

Aligned fibers could be different in diameter, different in material or other characteristics. If needed, the aligned fiber polymer could be different from the non-aligned fiber polymer. The aligned fiber polymer could be more or less bio-absorbable, dependent on the needs.

By using a bio-absorbable wire the circumferential strength at specific areas is enhanced. These wires will be absorbed over-time like the rest of the heart valve, but will give support during first ETR to prevent tears. An aligned wire could be sutured through the coaptation plane of the leaflets or attached in other ways. An aligned circumferential band which supports the leaflets will prevent tearing as well. Alternatively, an aligned edge or rim could be added during production or after production onto or into the scaffold, e.g. by directly electrospinning on the scaffold.

In one example, the aligned and non-aligned fibers could be woven and/or interconnected.

The method as shown in FIG. 3 has a second polymer source that is used to apply aligned fibers during the production in addition to non-aligned fibers produced by a first polymer source. These aligned fibers can be either electrospun using a separate power supply or pulled from a continuous droplet supplied by a pump. This results in a very accurate positioning in the deposition area. Using this method, one could spin specific orientations on complex shaped targets for making heart valves.

The electrospun material referenced in this document may comprise the ureido-pyrimidinone (UPy) quadruple hydrogen-bonding motif (pioneered by Sijbesma (1997), Science 278, 1601—1604) and a polymer backbone, for example selected from the group of biodegradable polyesters, polyurethanes, polycarbonates, poly(orthoesters), polyphosphoesters, polyanhydrides, polyphosphazenes, polyhydroxyalkanoates, polyvinylalcohol, polypropylenefumarate. Examples of polyesters are polycaprolactone, poly(L-lactide), poly(DL-lactide), poly(valerolactone), polyglycolide, polydioxanone, and their copolyesters. Examples of polycarbonates are poly(trimethylenecarbonate), poly(dimethyltrimethylenecarbonate), poly(hexamethylene carbonate).

The same result may be obtained with alternative, non-supramolecular polymers, if properties are carefully selected and material processed to ensure required surface characteristics. These polymers may comprise biodegradable or non-biodegradable polyesters, polyurethanes, polycarbonates, poly(orthoesters), polyphosphoesters, polyanhydrides, polyphosphazenes, polyhydroxyalkanoates, polyvinylalcohol, polypropylenefumarate. Examples of polyesters are polycaprolactone, poly(L-lactide), poly(DL-lactide), poly (valerolactone), polyglycolide, polydioxanone, and their copolyesters. Examples of polycarbonates are poly(trimethylenecarbonate), poly(dimethyltrimethylenecarbonate), poly (hexamethylene carbonate).

What is claimed is:

1. A method of electrospinning a heart valve leaflet, comprising:

(a) electrospinning aligned fibers onto a mandrel using a first source, wherein the aligned fibers are bioabsorbable polymer fibers; and (b) electrospinning non-aligned fibers onto the mandrel using a second source, wherein the second source electospins simultaneously with the first source and, wherein the non-aligned fibers are bioabsorbable polymer fibers, wherein the electrospinning of the aligned fibers includes electrospinning distinct patches or regions at the mandrel therewith producing a circumferentially aligned band of the heart valve leaflet, and wherein the aligned fibers and the non-aligned fibers at the distinct patches or regions are electrospun as either distinct layers or as an intermixed pattern.

2. The method as set forth in claim 1, wherein the bioabsorbable polymer fibers of the aligned fibers are supramolecular bioabsorbable polymer fibers and/or wherein the bioabsorbable polymer fibers of the non-aligned fibers are supramolecular bioabsorbable polymer fibers.

3. The method as set forth in claim 1, wherein the circumferentially aligned band is from commissure to commissure at or near the free edge of the heart valve leaflet, or wherein the circumferentially aligned band is used to reinforce a belly area of the heart valve leaflet.

4. The method as set forth in claim 1, wherein the bioabsorbable polymer fibers of the aligned fibers form a porous network to allow infiltration of cells, and wherein the porous network with infiltrated cells is replaced over time with newly formed tissue, and/or wherein the bioabsorbable polymer fibers of the non-aligned fibers form a porous network to allow infiltration of cells, and wherein the porous network with infiltrated cells is replaced over time with newly formed tissue.

5. A heart valve, comprising at least one leaflet, wherein a free edge of the leaflet consists essentially of a circumferentially aligned band of aligned electrospun fibers with non-aligned fibers, wherein the aligned fibers are bioabsorbable polymer fibers, wherein the non-aligned fibers are bioabsorbable polymer fibers, and wherein the aligned fibers and the non-aligned fibers at the free edge are intermixed.

6. The heart valve as set forth in claim 5, wherein the bioabsorbable polymer fibers of the aligned fibers are supramolecular bioabsorbable polymer fibers and/or wherein the bioabsorbable polymer fibers of the non-aligned fibers are supramolecular bioabsorbable polymer fibers.

7. The heart valve as set forth in claim 5, wherein the bioabsorbable polymer fibers of the aligned fibers form a porous network to allow infiltration of cells, and wherein the porous network with infiltrated cells is replaced over time with newly formed tissue, and/or wherein the bioabsorbable polymer fibers of the non-aligned fibers form a porous network to allow infiltration of cells, and wherein the porous network with infiltrated cells is replaced over time with newly formed tissue.

8. A heart valve, comprising at least one leaflet, wherein the leaflet belly area consists essentially of a circumferentially aligned band of aligned electrospun fibers with non-aligned fibers, wherein the aligned fibers are bioabsorbable polymer fibers, wherein the non-aligned fibers are bioabsorbable polymer fibers, and wherein the aligned fibers and the non-aligned fibers at the free edge are intermixed.

9. The heart valve as set forth in claim 8, wherein the bioabsorbable polymer fibers of the aligned fibers are supramolecular bioabsorbable polymer fibers and/or wherein the bioabsorbable polymer fibers of the non-aligned fibers are supramolecular bioabsorbable polymer fibers.

10. The heart valve as set forth in claim 8, wherein the bioabsorbable polymer fibers of the aligned fibers form a porous network to allow infiltration of cells, and wherein the porous network with infiltrated cells is replaced over time with newly formed tissue, and/or wherein the bioabsorbable polymer fibers of the non-aligned fibers form a porous network to allow infiltration of cells, and wherein the porous network with infiltrated cells is replaced over time with newly formed tissue.

* * * * *